United States Patent [19]

Stivanello

[11] Patent Number: 5,973,157

[45] Date of Patent: Oct. 26, 1999

[54] PROCESS FOR THE SYNTHESIS OF 1,7-DIARLY OR HETEROARYL-HEPTANE-4-OLS AND NEW SYNTHETIC INTERMEDIATES

[75] Inventor: Mariano Stivanello, Schio, Italy

[73] Assignee: F.I.S. Fabbrica Iltaliana Sintetici S.p.A., Vicenza, Italy

[21] Appl. No.: 09/062,610

[22] Filed: Apr. 20, 1998

[30] Foreign Application Priority Data

Apr. 18, 1997 [IT] Italy .................................. MI97A0912

[51] Int. Cl.$^6$ .................................................. C07D 213/30
[52] U.S. Cl. ............................................................ 546/255
[58] Field of Search ............................................... 546/255

[56] References Cited

FOREIGN PATENT DOCUMENTS

WO 95/26337  10/1995  WIPO .

OTHER PUBLICATIONS

J. Am. Chem. Soc., 1992, 114, 1091–1092.
EP SEarch Report dated Jul. 21, 1998.

*Primary Examiner*—Zinna Northington Davis
*Attorney, Agent, or Firm*—Diller, Ramik & Wight, PC

[57] ABSTRACT

This invention offers a process for the synthesis of a compound of the formula

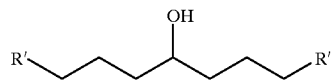

wherein R' is a phenyl, a substituted phenyl, a heterocyclic aromatic group, a heterocyclic aromatic substituted group, a linear or branched alkyl group, or a cycloalkyl group.

The invention also comprises the following compounds of a formula 1' and 2' as useful new synthesis intermediates.

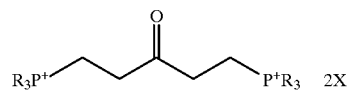

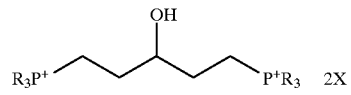

wherein R is a phenyl, a substituted phenyl, an alkyl, a cycloalkyl and X is Cl, Br, I, F, $CH_3SO_3$, p—$CH_3$—$C_6H_4$—$SO_3$.

4 Claims, No Drawings

PROCESS FOR THE SYNTHESIS OF 1,7-DIARLY OR HETEROARYL-HEPTANE-4-OLS AND NEW SYNTHETIC INTERMEDIATES

This invention relates to new chemical compounds, a process for their production and their application in the preparation of intermediates useful for the synthesis of pharmaceutical products.

The Wittig reactions and other correlated reactions are among the best known and well established processes for the normal and stereo-selective formation of double carbon-carbon bonds. The phosphonium salts and the corresponding phosphoranes can therefore be considered to be syntones useful for homologating the carbon atoms. Their application both in scientific research and in industrial processes is gaining an ever more widespread acceptance.

Among the innumerable phosphonium salts on the market or easily synthesized, a particular interest is arising for a salt of α,ω-biphosphonium of the following general formula:

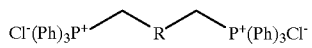

wherein R may be an alkylic chain, a general atom or a functional group.

These salts can therefore be considered as potential α,ω-syntones for the synthesis of substituted dienes.

This invention also proposes new compounds as syntones useful for a simple new method with a high yield for the synthesis of 1,7-diaryl or heteroaryl-heptane-4-ols of the general formula

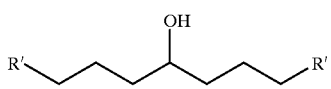

wherein R' is an aryl or heteroaryl group.

These 1,7-diaryl or heteroaryl-heptane-4-ols play an important role in the synthesis of a new series of "Cancer Multidrug Resistance (CMR) Chemosensitizers", recently developed by Vertex Pharmaceutical Inc. (PCT Int. Appl. WO 9526337, Oct. 15, 1995).

Among these, the heterocyclic 1,7-dipyridin-3-yl-heptane-4-ol 4 is the most interesting derivative:

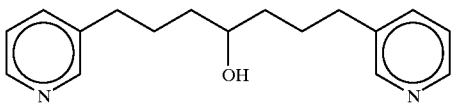

The most obvious approch to this class of secondary long chain alcohols is Grignard's (or a similar) reaction between a halogen of 3-aryl (heteroaryl) propyl-magnesium (or a corresponding organometallic compound) and a formic acid ester; however, the synthesis of these propyl halogens (in particular of those having a heteroarylic portion) is not always easy, and moreover, the organometallic reaction may occasionally be difficult.

Other methods of synthesis, well known to those having a common experience in the field, may be even more complex, involving a multistage synthesis and/or very special reagents and intermediates. Such methods can therefore be excluded, especially where an industrial process is to be developed.

In the Vertex patent mentioned above, the new intermediate 1,7-dipyridin-3-yl-heptane-4-ol 4 has for the first time been synthesized by adopting a two-stage system composed of:
1. Coupling, catalyzed by copper-palladium, of hepta-1,6-diyn-4-ol with 3-bromopyridin to obtain the 1,7-bipyridin-3-yl-hepta-1,6-diyn-4-ol, which is isolated by column chromatography with a rather good yield;
2. Platinum-oxide hydrogenation of the intermediate mentioned above, thus obtaining the 1,7-dipyridin-3-yl-heptane-4-ol 4 with a high yield.

In the patent mentioned above, the synthesis of the starting substance hepta-1,6-diyn-4-ol, not available on the market, is not described, but this substance can eventually be prepared by a synthesis similar to Grignard's reaction between an organometallic derivative of propargyl-bromide and ethyl-formiate; because of the propargyl-bromide's high reactivity this approach can be expected to be particularly difficult, in particular on an industrial basis.

In view of a future development, this synthesis presents a number of problems: highly expensive raw materials (3-bromopyridin, propargyl bromide, palladium dichloride, platinum oxide), probably difficult operating conditions (low temperature, absolutely anhydrous solvents), and a poorly efficient process.

The scope of this invention is to overcome all these problems by proposing a very effective new process, of low cost and easily developed to obtain the mentioned intermediate described as 1,7-dipyridin-3-yl-heptane-4-ol 4.

The process of the invention may also be applied in the synthesis of other 1,7-diaryl(heteroaryl)heptane-4-oles of the general type 3.

This invention describes a simple and effective process for Wittig's reaction, which avoids the use of a strong base (for example, n-butyl-lithium, lithium diisopropylamide, lithium hexamethyldisilazide, potassium-t-butoxide, sodium metoxide) and absolutely anhydrous conditions.

To achieve these objectives, this invention proposes a process for the synthesis of a compound of the formula:

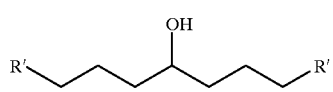

wherein R' is a phenyl, a substituted phenyl, a heterocyclic aromatic group, a heterocyclic aromatic substituted group, a linear or branched alkyl group, or a cycloalkyl group, comprising the following stages:
a) reacting a compound of the formula 5' with a phosphine $PR_3$ to form a compound 1', based on the reaction:

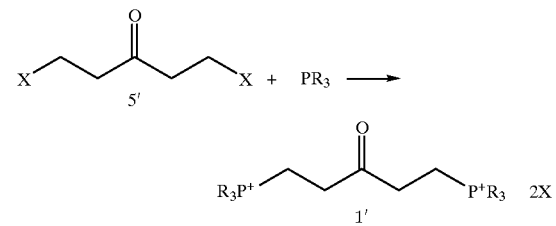

wherein R is a phenyl, a substituted phenyl, an alkyl, cycloalkyl and X is Cl, Br, I, F, $CH_3SO_3$, p—$CH_3$—$C_6H_4$—$SO_3$.
b) reducing said compound 1' with sodium borohydride, thus forming a compound 2', according to the reaction:

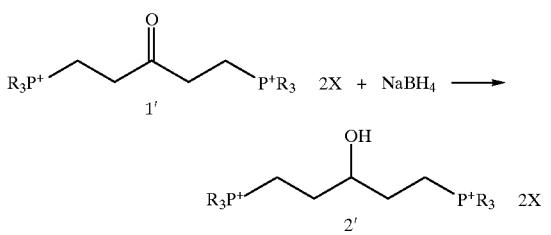

wherein R is a phenyl, a substituted phenyl, an alkyl, cycloalkyl and X is Cl, Br, I, F, CH$_3$SO$_3$, p—CH$_3$—C$_6$H$_4$—SO$_3$.

c) reacting said compound of formula 2' with a reagent chosen among 3-pyridincarboxaldehyde, benzaldehyde, a substituted benzaldehyde, an aromatic heterocyclic aldehyde, an alkyl aldehyde, or a cycloalkyl-aldehyde, thus obtaining a compound of the formula 6'

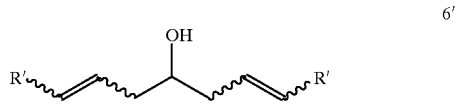

wherein R' has the same meaning as indicated above;

d) reducing said compound of the formula

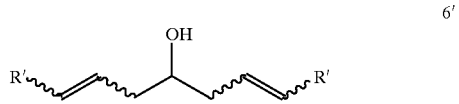

wherein R' has the same meaning indicated above, thus obtaining a compound of the formula

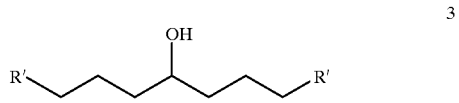

wherein R' has the same meaning described above.

The following is a detailed description of the process of the invention according to a particular form of execution.

1. SYNTHESIS OF 1,5-BIS (TRIPHENYLPHOSPHONIUM) PENTANE-3-ONE DICHLORIDE AND OF THE CORRESPONDING ALCOHOL

The new compound ,1,5-bis(triphenylphosphonium) pentane-3-one dichloride 1 can be prepared with a high yield by a simple two-stage process, as described in Scheme I:

SCHEME I

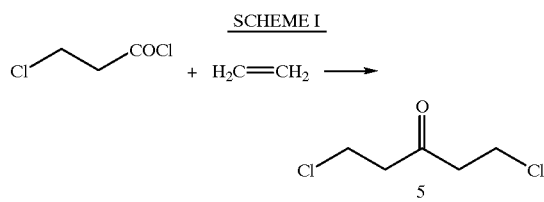

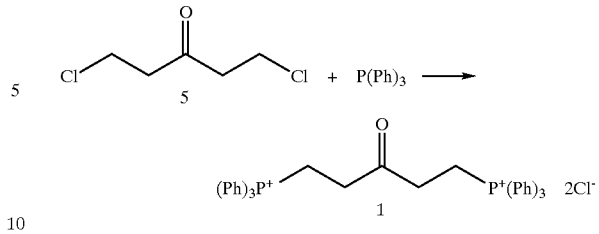

The intermediate 1,5-dichloropentane-3-one 5 is a well known com-pound easily synthesized in accordance with a normal Friedel-Craft acylation of ethylene with 3-chlorpropionylchloride, which is a low cost raw material available on the market.

The reaction conditions are essentially the same as described in the literature (see for example A. B. Smith III, M. Fukui, H. A. Vaccaro and J. R. Empfield, J.Am. Chem. Soc. 1991, 113, 2071–2092), by using anhydrous aluminum chloride with a catalyst, methylene chloride with a solvent and operating from 0° to +5° C. By optimizing the conditions of the reaction (namely concentration, time, speed of addition of the ethylene, cooling temperature), the 1,5-dichloropentane-3-one 5 can be isolated in the form of a raw dark red oil, with a quantitative yield and a purity of up to 96% (GC,area %).

It has been highlighted that this intermediate is fairly unstable during conservation or if subjected to a distillation at a rather elevated temperature. In the synthesis stage immediately following it may therefore be advisable to use the raw oil directly.

Despite the considerable number of publications and patents relating to the application of 1,5-dichloropentane-3-one (for example, in the synthesis of the tetrahydro-4H-pirane-4-one and the alkyl-substituted 4-piperidones), based on our knowledge its use as a starting substance for double Wittig reactions is still unknown.

On the other hand, the reaction of this intermediate with triphenylphosphine (2.0 equivalents), a suitable solvent and temperature has directly yielded the 1,5-bis (triphenylphosphonium) pentane-3-one dichloride 1.

The reaction can be carried out with a broad variety of solvents, from apolar solvents such as toluene up to aprotic polar solvents such as acetonitrile, acetone, 2-butanone, and N,N-dimethylformamide (DMF). The latter solvent proved to be the best: the biphosphonium salt is produced with a very high yield and purity, by simply mixing the two reagents and heating the reaction mixture to 80–100° C.

On a larger scale (0.5–1.0 moles of 1.5-dichloropentane-3-one), the reaction can suitably be prepared by adding the dichloroketone to a concentrated and preheated triphenylphosphine solution in DMF: the biphosphonium salt starts to precipitate during the addition of the dichloroketone, and may be isolated by filtration after cooling.

The 1,5-bis(triphenylphosphonium) pentane-3-one dichloride 1 can usually be obtained in the form of a white crystalline powder, with a high yield in the range of 90% to 95% (from the 3-chloropropionylchloride). This biphosphonium salt has a high degree of purity (over 98%, controlled by TLC and NMR), is not hygroscopic and is thermally stable; unfortunately, it was found to be easily decomposed under alkaline conditions, both in water (NaOH and Na$_2$CO$_3$ solutions) and in organic solvents (such as MeONa/MeOH, BuLi/THF), while giving off triphenylphosphine (an excellent exit compound) and forming divynilketone, an unstable product which further reacts as follows:

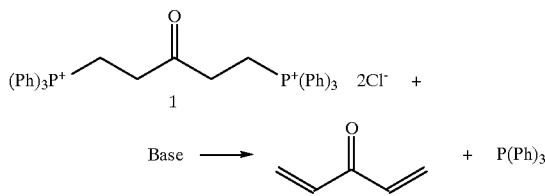

the intermediate 1,5-bis(triphenylphosphonium) pentane-3-one dichloride is therefore not suitable for Witting and similar reactions, which generally use alkaline conditions to produce the corresponding phosphorane.

Despite its instability, however, this compound may be reduced to the corresponding alcohol, namely the 1,5-bis (triphenylphosphonium)-pentane-3-ol dichloride 2, a new compound as shown in Scheme II:

SCHEME II

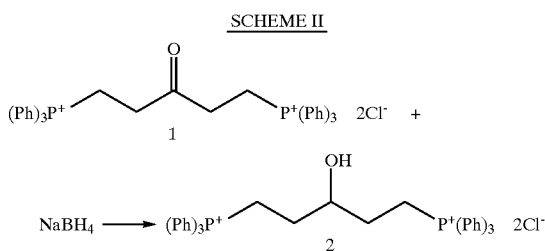

The easiest method to effect this reduction is to add a stechiometric quantity (0.25 mole equivalents) of sodium borohydride to a cold aqueous solution of the bis (triphenylphosphonium) pentanone 1; the reaction is very quick even at 5–10° C. and approximately quantitative; the only impurity is a small amount of triphenylphosphine (about 1–3 mole-equivalent %), formed by a slight decomposition of the fairly basic compound due to the alkaline sodium borohydride. The diphosphonium pentanol can be suitably isolated from the reaction mixture by adding excess acetone (to decompose the unreacted sodium borohydride), acidifying to a pH 3 (to decompose the trialkoxyborate compound eventually formed), filtering off the triphenylphosphonium, partially vacuum-concentrating the aqueous solution and extracting it with a polar solvent such as methylene chloride or ethyl acetate, thus obtaining a colorless oil which crystallizes if left quiescent.

The 1,5-bis (triphenylphosphonium) pentane-3-ole dichloride 2 is isolated in a nearly quantitative manner in the form of a hygroscopic white crystalline solid showing a good degree of purity (TLC, NMR): it is indefinitely stable if kept under cover in the absence of humidity.

This intermediate product can also be isolated directly, by completely concentrating the aqueous solution and using the residual oil as such in the synthesis stage immediately following; this avoids any solvent extraction, a troublesome industrial process also involving a rather large volume of solvent.

2. DOUBLE WITTIG REACTION OF 1,5-BIS (TRIPHENYLPHOSPHONIUM) PENTANE-3-OL DICHLORIDE: SYNTHESIS OF 1.7-DIPYRIDIN-3-YL-HEPTANE-4-OL The action of 2.0 equivalents of a suitable base of 1,5-bis (triphenyl-phosphonium) pentane-3-ol dichloride 2 should formally lead to the 1,5-bis (triphenylphosphoranylidene) pentane-3-ol 7:

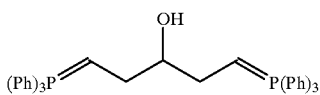

This γ-oxide-bisilide is not known in the literature, where on the contrary simple bisilides are found (for instance, the stable 1,3-bis(triphenylphosphoranylidene)acetone or the unstable ilides obtained from linear alkyl-bisphosphonium salts) or simple mono γ-oxide-ilides (for instance the 3-triphenylphosphoranylidene-propanol) [for a review of Witting and similar olefination reactions see B. E. Maryanoff and A. B. Reitz, Chem. Rev., 1989, 89, 863–927; for the bis-ilides see for example H. J. Bestman and W. Schlosser, Synthesis, 1979, 210,202; for the oxide-ilides see for example B. E. Maryanoff et al., J.Am. Chem. Soc. 1985, 107, 217–226].

The deprotonation of mono γ-oxide phosphone salt is carried out in the literature with strong bases, as normally employed in the classic Wittig reactions (for example with potassium t-butoxide, n-butyllithium, lithium hexamethyldisilazide, sodium hydride): the reaction with benzaldehyde prevalently supplies the corresponding E-alkene with molar yields in the range of 35% to 80%, depending on the quantity and type of the base used.

All attempts at a double deprotonation of the 1,5-bis (triphenylphos-phonium)-pentane-3-ol 2 with 2 or more equivalents of each of the abovementioned bases, in the absence or presence of 3-pyridenecarboxaldehyde (nicotinaldehyde) have been completely devoid of favourable results, leading to a broad decomposition of the biphosphonium salt, combined with the formation of triphenylphosphine.

The Applicant has on the other hand achieved fairly favourable results by adopting a solid-liquid technique developed by a group of Frenchmen a few years ago [M. Delmas et al., Synth. Commun., 16, 1617–1620 (1986)]. This process utilizes anhydrous potassium carbonate with an isopropanol reflux to carry out a Wittig reaction between the 3-hydroxypropyl-triphenylphosphonium and aromatic aldehydes with high molar yields (52–92%).

The above mentioned process applied to the applicant's substrates leads to the intermediate product constituted by the 1,7-dipyridin-3-yl-hepta-1,6-dien-4-ole 6 in the form of a mixture of 3 isomers (E,E+E,Z+Z,Z) in accordance with the scheme III:

SCHEME III

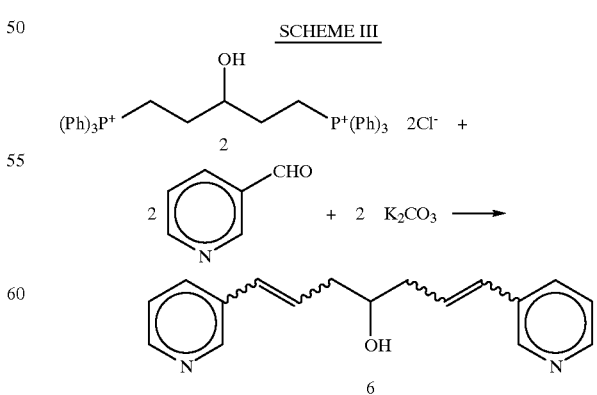

The reaction is unfortunately incomplete even with an excess of K2C03 and after a long refluxing period; morover, the analysis reveals a number of impurities of the raw product. A considerable improvement can be obtained simply by changing the given alcohol (isopropanol) solvent with an aprotic polar solvent, for example N,N-dimethylformamide (DMF): the potassium carbonate exhibits an increased alkalinity in DMF compared to the isopropanol, while still remaining a low alkalinity product.

The above reaction can be carried out simply by mixing equi-molar quantities of raw 1,5-bis(triphenylphosphonium)pentane-3-ol dichloride 2 (1.0 mole equivalents), pyridin-3-carboxyaldehyde (nicotinic aldehyde, 2.0 mole equivalents) and anhydrous potassium carbonate (2.0 mole equivalents) in DMF; and heating the mixture to a temperature above 80° C. for the time needed to achieve an almost complete conversion (over 95%).

The best results are obtained by using a dehydrated 1,5-bis(triphenylphosphonium)pentane-3-ol dichloride 2; this can be achieved by stripping the raw oil with DMF under vacuum. It is important to highlight the total absence of degradation of the γ-oxide-bisilide 5 formed in-situ, even after a prolonged reaction time (up to 24 hours at 80–90° C.).

Moreover, the HPLC analysis of the raw product does not evidence any impurity apart from a small quantity of unreacted nicotinic aldehyde and a reaction intermediate, namely the following mono-substituted derivative:

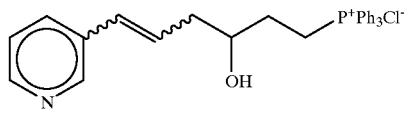

The reaction process is also simple and comprises: vacuum distillation of the solvent (for DMF recycling), extraction of the raw residual with a suitable organic solvent, aqueous rinsing of the organic phase and final extraction of the product with acid water to remove the triphenylphosphine oxide, which is a byproduct of the Wittig reaction.

The acidic aqueous solution may be used directly in the last stage of the synthesis, meaning the reduction of the double bond leading to the corresponding saturated compound 1,7-dipyridin-3-yl-heptane-4-ol 4, according to the scheme IV:

SCHEME IV

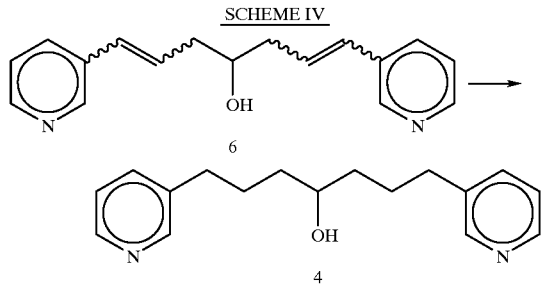

This reduction can easily be carried out by a catalytic hydrogenation, using common palladium on carbon as a catalyst, for example Pd/C with 5% moisture; the reaction is fast and always quantitative even at room temperature, under a moderate hydrogen pressure (below 5 bar) and in the presence of a small quantity of catalyst.

The raw reaction product is also free of impurities, without any isomerization of double bonds, or a presence of byproducts owing to hydrogenolysis.

Even in this case, the operations required for the reaction process are elementary: after filtering off the catalyst, the filtrate can be raised to a pH above 8 by a concentrated solution of sodium hydroxide, and the raw end-product can be extracted with a suitable solvent; the organic phase is then concentrated, thus obtaining the raw 1,7-dipyridin-3-yl-heptane-4-ol 4 in the form of an orange-colored oil, contaminated by a small quantity of 3-hydroxymethylpyridin.

The raw product may be purified by the crystallization of an appropriate salt; the process may, for example, be applied to the dichlorohydrate salt prepared with gaseous hydrochloric acid in an anhydrous polar solvent.

The 1,7-dipyridin-3-yl-heptane-4-ol 4 dichlorohydrate can be isolated in the form of a slightly hygroscopic, pale yellow solid crystalline product with a purity in the range of 98–99%; an appropriate recrystallization can also attain a product of greater purity (a degree of purity exceeding 99% as determined by HPLC).

The molar yield of the above preparation, starting from 1,5-bis(tri-phenylphosphonium)-pentane-3-one dichloride 1 is about 70%, and the overall yield of the entire synthesis (that is, from 3-chloropropionyl chloride) is in the range of 60–65%.

This invention can also be applied to the synthesis of other symmetrically substituted 1,7-diaryl- or heterodiaryl heptane-4-ols; these derivatives can be isolated by using normal purification methods, well known to the experts in organic chemistry, which involve crystallization processes or column chromatography.

In summarizing the general advantages of the invention, it can be said to offer (with reference to the particular form of execution described above):

1. A method for preparing the new intermediate 1,5-bis(triphenylphospho-nium) pentane-3-one dichloride 1 by starting from 3-chloropropionylchloride, ethylene and triphenylphosphine, all easily available and inexpensive raw materials, characterized by a high overall yield and by a simple process;

2. A method for preparing, with a high yield, the new intermediate 1, 5-bis (triphenylphosphonium)pentane-3-ol dichloride 2 by reduction with NaBH4 of the corresponding ketone 1;

3. A single-phase process in three passages for preparing the desired compound, namely 1,7-dipyridin-3-yl-heptane-4-ol 4 from the biphosphonium salt 1, composed of the following stages:

b. reducing the intermediate of formula 1 to the corresponding raw intermediate of formula 2, c. reacting the raw intermediate 2 with pyridin-3-carboxaldehyde in a typical Wittig reaction in DMF by using potassium carbonate as a base, thus obtaining the raw intermediate 1,7-dipyridin-3-yl-hepta-1,6-dien-4-ol 6 in the form of a blend of isomers;

d. reducing the above intermediate of formula, 6 by a catalytic hydrogenation, thus obtaining the 1,7-dipyridin-3-yl-heptane-4-ol 4, which is finally isolated and purified by a suitable salt, for example by the chlorohydrate salt, with a high overall yield and a high degree of purity.

This reaction therefore offers a general method for preparing symmetrically substituted 1,7 diaryl- or heterodiaryl-heptane-4-ols, useful as pharmaceutical intermediates, especially for enlargements on an industrial scale, with a high overall yield and by using inexpensive raw materials available on the market.

In order to describe this invention in even greater detail, the following non-limiting examples are given.

EXAMPLES

GENERAL METHODS

The nuclear protonic ($^1$H-NMR) magnetic resonance spectra were recorded on a Varian Gemini 2000 spectrometer, operating at 300 Mhz; the chemical shifts are reported in δ (ppm) with respect to an internal TMS (tetramethylsilane) standard. Th HPLC analyses were performed on a Hewlett Packard 1050 liquid-phase chromatograph, and the GLC analyses on a Hewlett Packard 5890 II gas chromatograph.

Example 1
1,5-DICHLOROPENTANE-3-ONE 5

A suspension of anhydrous aluminum (146.6 g, 1.10 moles) in methylene chloride (600 ml) was cooled to 0° C. in a nitrogen atmosphere: 3-chloropropionyl-chloride (127.0 g, 1.00 moles) was added dropwise while agitating for about 30 minutes. Gaseous ethylene was bubbled through the turbid suspension for a period of 2–3 hours, while maintaining the temperature below 5° C.: the progress of the reaction was controlled by GLC. The clear mixture thus obtained was then poured into a pre-cooled solution of concentrated hydrochloric acid (130 ml) in water (400 ml), while maintaining the temperature below 10° C. throughout the cooling process. The two-phase mixture was agitated for about 30 minutes, the aqueous layer was separated, the organic phase was washed with water (250 ml) and concentrated under vacuum at 20–25° C., thus obtaining the raw 1,5-dichloropentane-3-one 5 in the form of dark red oil (175 g, a yield superior to the theoretical value), with a GLC purity of 90–95%.

Example 2
1,5-BIS(TRIPHENYLPHOSPHONIUM)PENTANE-3-ONE DICHLORIDE 1

A solution of 262 g of triphenylphosphine (1.00 moles) in N,N-dimethylformamide (500 ml), preheated to 90° C. in a nitrogen atmosphere was added to a solution of raw 1,5-dichloropentane-3-one (87.5 g, half the quantity with respect to that of the above mentioned preparation, 0.50 theoretical moles) in DMF (100 ml) in about 2 hours. The resulting suspension was subjected to an agitation at 90° C. for two hours, cooled to 20° C. and agitated again for 1 hour. The precipitate was filtered, washed with acetone and dried at 40–50° C. to a constant weight, thus obtaining 310–320 g of 1,5-bis(triphenylphosphone)pentane-3-one dichloride 1, a white crystalline solid. Yield: 91–95%, melting point= 214–217° C., $^1$H-NMR (CDCl$_3$, TMS), δ: 3.35 (m complexed, 4H, H$_2$ and H$_4$) , 3.92 (m complexed, 4H, H$_1$ and H$_5$), 7.65–7.85 (m complexed, 30 H, aromatic protons).

Example 3
1,5-BIS (TRIPHENYLPHOSPHONIUM) PENTANE-3-OL DICHLORIDE 2

A solution of 1,5 bis (triphenylphosphonium)pentane-3-one dichloride 1 (200.0 g, 0.296 moles) in water (200 ml) was added to a solution of sodium borohydride (3.40 g, 0.090 moles) in water (20 ml) over 30 minutes and at a temperature in the range of 10–15° C. The resulting white suspension was subjected to an agitation at 15° C. for another hour and treated with acetone (20 ml). The reaction mixture was agitated for another 30 minutes, and the pH was adjusted to about 4.0 with concentrated hydrochloric acid (30 ml): the triphenyl-phosphate byproduct was filtered off and the filtrate was concentrated under a vacuum at 60° C./20 mbar, thus obtaining a pale yellow oil which was dehydrated by stripping it with DMF (2×200 ml).

Alternatively, the raw oil can be extracted with methylene chloride (3×300 ml), and the organic solution can be vacuum- concentrated to obtain about 200–210 g of raw 1,5 bis (triphenylphosphonium)pentane-3-ol dichloride 2, in the form of a colorless oil, which crystallized if left quiescent or treated with ethyl-acetate (200 ml). The resulting white solid was hygroscopic, which made it impossible to carry out routine analyses. The HPLC purity (area %) was 98.5%. $^1$H-NMR (CDCl$_3$, TMS), δ: 1.80–2.10 (m complexed, 4H, H$_2$ and H$_4$), 2.7–3.5 (s enlarged, 1H, OH), 3.65 (q complexed, 2H, H$_2$, and H$_4$), 3.85 (q complexed, 2H, H$_2$ and H$_4$), 4.19 (t enlarged, 1H, H$_3$), 7.65–7.85 (m complexed, 30H, aromatic protons).

Example 4
1,7-DIPYRIDIN-3-YL-HEPTA-1,6-DIEN-4-OL 6

A solution of raw anhydrous 1,5 bis (triphenylphosphonium)pentane-3-ol dichloride 2 (about 200–210 g, 0.296 moles) in DMF (400 ml) was added to pyridin-3-carboxaldehyde (62.8 g, 0.60 moles) and anhydrous potassium carbonate (90.0 g, 0.65 moles). The two-phase mixture was heated to 80–90° C. and subjected to agitation for 15–20 hours, until the rate of transformation exceeded 95% (HPLC). The resulting orange-colored suspension was cooled to about 60° C., the solvent was removed under vacuum at 65° C./20 mbar and the pasty residual was taken up with ethyl acetate (400 ml) and water (400 ml); the two-phase mixture was subjected to agitation at 20–30° C. for 15–20 minutes, until the inorganic salts were completely dissolved. The organic phase was separated and the aqueous layer extracted with ethyl acetate (200 ml); the joint organic phases were extracted with aqueous 10% sulfuric acid (150+30 ml); the organic phase containing the triphenylphosphine byproduct was discarded and the aqueous acid solution was used as such in the immediately following stage. The HPLC analysis (area %) was 90%.

Example 5
1,7 -DIPYRIDIN-3-YL-HEPTANE-4-OL 4

The above solution was introduced into a stainless steel autoclave, adding Pd/C with 5% moisture (8.0 g, H$_2$O 50%, 5% by weight, dry). The container was purged with nitrogen and subjected to a 5 bar gaseous hydrogen pressure. The hydrogenation was carried out at 20° C. for about 8 hours or in any case until all the hydrogen had been consumed. The autoclave was then purged with nitrogen, the catalyst was filtered off, ethyl acetate (400 ml) was added to the yellow-colored solution, and the pH was raised above 9 by using a 30% sodium hydroxide solution (about 100 ml). The organic phase was separated and the aqueous phase was extracted with ethyl acetate (200 ml); the collected organic phases were washed with water (100 ml), treated with activated carbon (10 g), filtered and vacuum-concentrated at 40° C./20 mbar to obtain 72–78 g of raw 1,7-dipyridin-3-yl-heptane-4-ol 4, a viscous oil of orange color, Molar yield: 90–98% (from the biphosphonium salt 1); the HPLC analysis (area %) was 88–90%, with 6–8% of 3-hydroxymethylpyridine.

The raw oil mentioned above was dissolved in methylated ethanol (200 ml): gaseous hydrochloric acid was bubbled through this solution until reaching a pH below 3, while maintaining the temperature at 40–50° C.; ethyl acetate was added dropwise, and the resulting suspension was cooled to 20° C. and agitated for 2–3 hours. The precipitate was filtered off, washed with a 2:1 ethyl-acetate/ethanol mixture and dehydrated at 50° C. for about 8 hours, thus obtaining 68–72 g of the bichlorohydrate salt of 1,7-dipyridin-3-yl-heptane-4-ol 4 in the form of a solid crystalline product of yellowish color. Typical yield: 67–72%; HPLC analysis (area %): 98.0–98.5%.

This product can be re-crystallized as described above from a 2:1 ethyl acetate/ethanol mixture, with a typical crystallization yield of 90–93% and an HPLC purity in the range of 99.0 and 99.5%. Melting point: 146–147° C. An analysis by titration (AgNo3) gave 99.0% (corresponding to a molecular weight of 343.4). $^1$H-NMR (CD$_3$OD, TMS), δ: 1.52 (m complexed, 4H, H$_3$ and H$_5$), 1.83 (m complexed, 4H, H$_2$, and H$_6$), 2.92 system (A, A', 4H, H$_1$ and H$_7$), 3.65 (septet 1H, H$_4$, J=4.1), 5.00 (s enlarged, about 3H, OH and pyridinium H), 8.06 (dd, 1H, H$_5$, J$_{4,5}$=8.2, J$_{5,6}$=5.9) 8.59 (dt, 1H, H$_4$, J$_{4,6}$=J$_{2,4}$=1.5), 8.74 (d, 1H, H$_6$), 8.81 (d, 1H, H$_2$)

I claim:

1. A process of preparing a compound of the formula

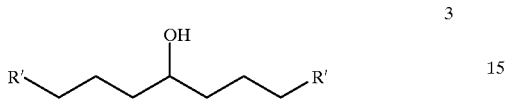

wherein R' is a phenyl, a substituted phenyl, a heterocyclic aromatic group, a heterocyclic aromatic substituted group, a linear or branched alkyl group, or a cycloalkyl group, comprising the following stages: p1 a) reacting a compound of the formula 5' with a phosphine PR$_3$ to form a compound 1', based on the reaction:

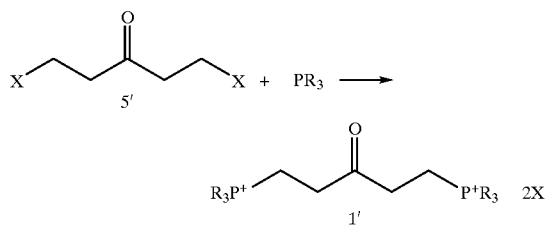

wherein R is a phenyl, a substituted phenyl, an alkyl, cyclo-alkyl and X is Cl, Br, I, F, CH$_3$SO$_3$, p—CH$_3$—C$_6$H$_4$—SO$_3$ b) reducing said compound 1' with sodium borohydride, thus forming a compound 2', according to the reaction:

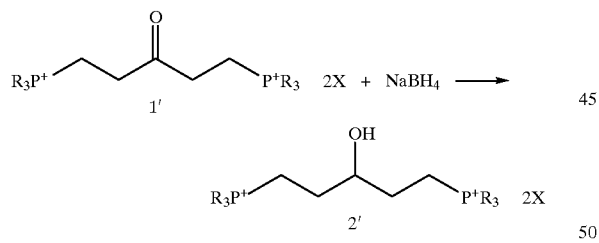

wherein R is a phenyl, a substituted phenyl, an alkyl, cyclo-alkyl and X is Cl, Br, I, F, CH$_3$SO$_3$, p—CH$_3$—C$_6$H$_4$—SO$_3$ c) reacting said compound of formula 2' with a reagent selected from 3-pyridincarboxaldehyde, benzaldehyde, a substituted benzaldehyde, an aromatic heterocyclic aldehyde, an alkyl aldehyde, or a cyclo-alkylaldehyde, thus obtaining a compound of the formula 6'

wherein R' has the same meaning as indicated above;

d) reducing said compound of the formula

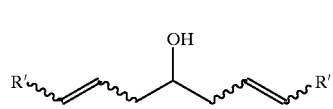

wherein R' has the same meaning indicated above, thus obtaining a compound of the formula

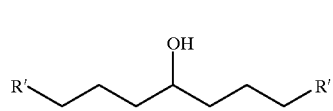

wherein R' has the same meaning described above.

2. Process according to claim 1 wherein stage c) is operated in the presence of an anhydrous potassium carbonate base, in an aprotic polar solvent selected from N,N-dimethylformamide, N, N-dimethylacetamide, N-methyl-2-pyrrolidinone, at a temperature in the range of 20° C.–150° C.

3. Process according to claim 1 wherein stage d) is operated under hydrogen pressure, in the presence of one of palladium on carbon, platinum on carbon, oxide on platinum, or Raney nickel as a catalyst, in a suitable organic solvent or water.

4. Process according to claim 1, including the following stages:

a) reacting the 1,5-dichloropentane-3-one of formula 5 with triphenylphosphine, thus forming 1,5-bis (triphenylphosphonium)pentane-3-one dichloride of formula 1, based on the reaction:

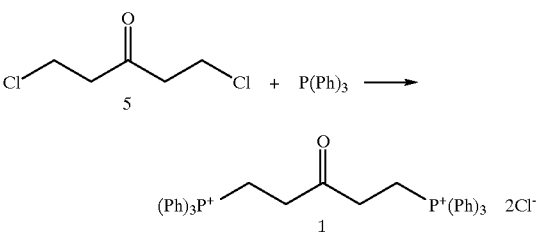

b) reducing said compound 1 with sodium borohydride, thus forming a compound 1,5-bis (triphenylphosphonium)pentane-3-ol dichloride of formula 2

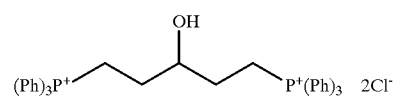

c) reacting said compound of formula 2 with 3-pyridincarboxaldehyde to obtain 1,7-dipyridin-3-yl-hepta-1,6-dien-4-ol of formula 6

13                                                14
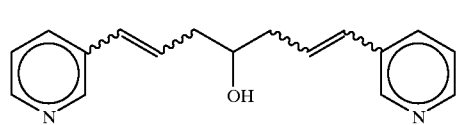
d) reducing said compound of formula 6 to obtain 1,7-
dipyridin-3-yl-heptane-4-ol 4
\* \* \* \* \*